United States Patent [19]

Ten Haken et al.

[11] 4,441,912

[45] Apr. 10, 1984

[54] N-PYRAZINYL-N-BENZYLCARBAMATES, HAVING FUNGICIDAL AND PLANT GROWTH REGULATING PROPERTIES

[75] Inventors: Pieter Ten Haken, Eastling, Nr. Faversham; Shirley B. Webb, Sheldwich, Nr. Faversham, both of England

[73] Assignee: Shell Oil Company, Houston, Tex.

[21] Appl. No.: 403,943

[22] Filed: Jul. 30, 1982

Related U.S. Application Data

[60] Division of Ser. No. 269,174, Jun. 2, 1981, Pat. No. 4,359,576, which is a continuation-in-part of Ser. No. 164,975, Jul. 1, 1980, abandoned.

[30] Foreign Application Priority Data

Jul. 19, 1979 [GB] United Kingdom ................. 7925164

[51] Int. Cl.$^3$ ..................... A01N 55/02; A01N 43/60; C07F 15/02; C07F 3/04
[52] U.S. Cl. ........................................................ 71/92
[58] Field of Search ............................................ 71/92

[56] References Cited

U.S. PATENT DOCUMENTS 3,880,840  4/1975  Field ................... 544/336

Primary Examiner—Mark L. Berch

[57] ABSTRACT

Certain N-(2-pyrazinyl)-N-benzylcarbamates, having fungicidal and plant-growth regulating properties.

2 Claims, No Drawings

N-PYRAZINYL-N-BENZYLCARBAMATES, HAVING FUNGICIDAL AND PLANT GROWTH REGULATING PROPERTIES

This application is a division of allowed application Ser. No. 269,174, filed on June 2, 1981, now U.S. Pat. No. 4,359,576, which was a continuation-in-part of application Ser. No. 164,975, filed on July 1, 1980, abandoned.

DESCRIPTION OF THE INVENTION

It has been found that useful fungicidal and plant growth regulating properties are possessed by N-pyrazinyl-N-benzylcarbamates, described by the formula

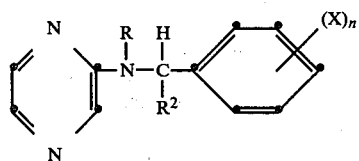

wherein R is the acyl moiety,

of certain aliphatic, and cycloaliphatic acids, $R^2$ is hydrogen or alkyl of one to four carbon atoms, n is one or two, and X is halogen or alkyl of one to six carbon atoms, and the acid addition salts, metal salt complexes and N-oxides thereof.

The moiety $R^1$ suitably is hydrogen, or is an alkyl, alkoxy-alkyl, cycloalkyl or alkylcycloalkyl moiety containing up to six carbon atoms.

Of particular interest because of its plant growth regulating properties is the individual species wherein R is tertiary-butyl, $R^2$ is hydrogen and $(X)_n$ is 4-chloro.

Compounds of Formula I form N-oxides; acid addition salts with acids, for example material acids such as sulphuric or hydrochloric acid or organic acids such as citric or tartaric acid; and complexes with metal salts, for example complexes of the compound of Formula I with a salt, for example a halide, of calcium, copper or iron, in the ratio of 2:1, 1:1 or 2:1, provided that they are horticulturally acceptable. The use of such derivatives forms part of the present invention, and the derivatives may be prepared from compounds of Formula I by methods analogous to known methods.

Compounds of the invention can be used to regulate growth of plants. Amongst the plant growth regulating properties which have been exhibited by various compounds of Formula I, are reduction in growth of plants, the production of very dark green leaves, enlarged cotyledons, and the production of shorter, broader leaves. These properties may for example be harnessed in the following applications, using certain compounds under certain conditions: reduction of growth of plants to alleviate stress in plant tissue, or to prevent lodging in tall plants such as cereals; increase in photosynthesis per unit area as a result of the production of very dark green leaves, giving better growth under poor light conditions; production of silage crops having a lower than normal water content; shape control in horticultural crops such as chrysanthemums and poinsettias; prevention of growth of unproductive flowers or runners in crops such as cotton, tobacco, lucerne, sugar beet or strawberries; and sugar cane ripening by prevention of growth at the end of the season. Certain of the compounds may also act to increase the yield of crops such as soyabeans.

Certain of the compounds of Formula I may be useful as "herbistats": application of the compound to the plants, seed, or the soil in which the plants are growing or are to be grown, results in much reduced growth of the plants. This is useful, for example, in controlling the ground cover vegetation in plantations and orchards, in controlling aquatic vegetation, for example in cereals, and in reducing the cutting frequency of grassy areas ("chemical lawn mowing").

Under certain circumstances, the plant growth regulating effects of compounds of Formula I, which are often very long lasting, can be amended or reversed by application of plant hormones such as auxins, cytokinins, phytosterols and, especially, gibberellic acid. Possible uses of this effect may, for example, include seed treatments: seeds of crops may be coated with gibberellic acid and sown normally. When the crop area is then treated with a compound of Formula I having "herbistat" or herbicidal properties the growth of weeds is inhibited, but because of their local environment of gibberellic acid, the growth of the crop seed is not affected. This may be useful in crops such as sugar beet, where the annual sugar beet which occurs as a weed is virtually impossible to combat by conventional herbicide treatment.

Certain commercial plant growth regulating compounds have a tendency to produce plants which are very susceptible to fungal attack. Thus the use as a plant growth regulator of a compound having both plant growth regulating and fungicidal activity would have obvious advantages.

In the method according to the invention, the compound of Formula I or acid addition salt, N-oxide or metal salt complex thereof, is suitably applied to the locus to be treated at a dosage in the range of from 0.1 to 3 kilogram per hectare. Most conventiently it is applied in the form of a composition containing the compound together with one or more suitable carriers.

Compounds of the invention can be prepared by acylating a compound of the general formula

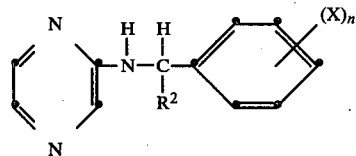

in which X, $R^2$ and n have the meanings given for the compounds of Formula I, using a suitable acylating agent.

Any suitable acylating agent, for example a carboxylic acid or an acid anhydride or, preferably, acid halide, derived from a carboxylic acid, may be used. Acid chlorides are especially suitable, and the reaction is then preferably carried out in the presence of an acid binding agent, which may be an organic or inorganic base. Organic amines, for example triethylamine, are especially suitable acid-binding agents. The reaction is preferably carried out in the presence of an inert solvent, for example a hydrocarbon such as benzene, at a temperature in the range of from 50° to 150° C., preferably 60° to 100° C. The reaction is conveniently carried out under reflux.

The compund of Formula II may for example be prepared by reduction of a compound of the general formula

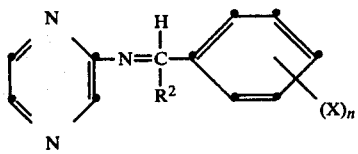

in which X, $R^2$ and n have the meanings given for the compounds of Formula I. The reduction may for example be carried out using gaseous hydrogen and a catalyst, or using formic acid. When formic acid is used the reaction conditions may be chosen such that at least some of the compound of Formula II produced is formylated in situ, thus directly producing a compound of Formula I in which R represents a formyl group starting from a compound of Formula III.

The compound of Formula III may be prepared by methods analogous to methods known in the art, for example by coupling a compound of the general formula

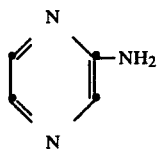

with a compound of the general formula

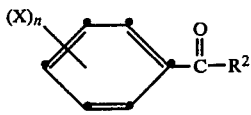

As stated above the method of regulating plant growth according to the invention is suitably carried out using a composition which comprises the active compound together with a suitable carrier. The invention therefore also provides a biologically active composition which comprises a novel compound according to the invention together with a suitable carrier. Preferably the amount of active ingredient in the composition is in the range of from 0.05 to 95% by weight of the composition.

A carrier in a composition according to the invention is any inert material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating agricultural compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaloinites, montmorillonites and micas; calcium carbonate; calcium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilizers, for example superphosphates.

Suitable liquid carriers include water; alcohols for example isopropanol and glycols; ketones, for example acetone, methyl ethyl ketone, methzl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 and 75% w of active ingredient and usually contain, in addition to solid inert carrier, 3–10% w of a dispersing agent and, where necessary, 0–10% w of stabilizer(s) and/or other additives such as penetrants or stickers. Dusts are usually formulated as a dust concentrate having a similar compositions to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–25% w active ingredient and 0–10% w of additives such as stabilizers, slow release modifiers and binding agents. Emulsifiable concentrates usually contain, in addition to a solvent and, when necessary, co-solvent, 10–50% w/v active ingredient, 2–20% w/v emulsifiers and 0–20% w/v of other additives such as stabilizers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The compositions of the invention may also contain other ingredients, for example, other compounds possessing insecticidal, herbicidal, plant growth regulating or fungicidal properties.

The following Examples illustrate the invention. In each of these examples, the identity of each intermediate and product was confirmed by appropriate chemical and spectral analyses.

EXAMPLE 1

N-t-butylcarbonyl-N-(4'-chlorophenylmethyl-)aminopyrazine (1)

(a) To a suspension of 21.75 g of 4-chloro-(pyrazineiminomethyl)benzene in 50 ml of dry toluene was added 10.8 g of 98% formic acid, and the mixture was stirred and heated under reflux for 16 hours. Toluene and formic acid were removed under reduced pressure and to the residue was added 100 ml of 10% hydrochloric acid. After extracting with 100 ml of toluene, the aqueous layer was separated and made alkaline by the addition of a concentrated aqueous solution of potassium hydroxide. The product was extracted into diethyl ether, and the extracts dried (MgSO$_4$). After removal of solvent, the product was purified by column chromatography (neutral alumina/diethyl ether as eluent). N-(4'-chlorophenylmethyl)-aminopyrazine (1A) was obtained, as a colorless material, m.p.: 86°–87° C.

(b) To a stirred solution of 2.2 g of 1A in 30 ml of dry benzene was added a solution of 1.4 g of trimethylacetylchloride of 10 ml of dry benzene followed by a solution of 1.3 g of dry triethylamine in 10 ml of dry benzene. The mixture was stirred and heated under reflux for 22 hours. After cooling, the reaction mixture was washed three times with water and dried (MgSO$_4$). Solvent was removed under reduced pressure and the residue was subjected to column chromatography on neutral alumina, eluting with diethyl ether/hexane (3:1), to give 1, as a colorless solid, m.p.: 65°–8° C.

EXAMPLES 2 TO 11

Using methods analogous to those described in Example 1 the following further individual compounds of the invention were prepared.

TABLE I

| In Formula I: Example No. | $(X)_n$ | R | $R^2$ | Melting Point °C. |
|---|---|---|---|---|
| 2 | 4-fluoro- | —CO.t-butyl | H | 41–42 |
| 3 | 4-chloro- | —CO—CH$_2$—t.-butyl | H | 53–55 |
| 4 | 4-chloro- | —CO—cyclopropyl(CH$_3$) | H | Oil |
| 5 | 4-chloro | —CO—CH$_2$—OCH$_3$ | H | Oil |
| 6 | 4-chloro | —CO.CH$_3$ | H | Oil |
| 7 | 3,4-dichloro | —CO—t.butyl | H | 71–73 |
| 8 | 4-methyl- | —CO—t.butyl | H | 79–80 |
| 9 | 2,4-dichloro | —CO—t.butyl | H | Oil |
| 10 | 4-chloro | —CO—cyclohexyl | H | Oil |
| 11 | 4-chloro- | —CO—CH$_2$.CH$_3$ | H | Oil |
| 12 | 4-chloro- | —CO—CH.(CH$_3$)$_2$ | H | 91–92 |
| 13 | 4-chloro | —CO—(CH$_2$)$_2$CH$_3$ | H | 58–60 |
| 14 | 4-chloro | —CO—CH$_2$.CH—(CH$_3$)$_2$ | H | 84–86 |
| 15 | 4-chloro | —CO—(CH$_2$)$_4$.CH$_3$ | H | 29–30 |
| 16 | 4-chloro | —CO(CH$_2$)$_3$.CH$_3$ | H | 60–62 |

EXAMPLES 17–19

By methods analogous to known methods, the following derivatives were prepared from compounds of formula I.

| Example No. | Compound | Melting Point °C. |
|---|---|---|
| 17 | N—oxide of the compound of Example 7 | 106–109 |
| 18 | N—oxide of the compound of Example 1 | 121–123 |
| 19 | Complex of two moles of the compound of Example 1 per mole of copper II chloride | 145–147 |

EXAMPLE 20

Herbicidal Activity

To evaluate their herbicidal activity, compounds according to the invention were tested using on a representative range of plants: maize, *Zea mays* (Mz); rice, *Oryza sativa* (R); barnyard grass, *Echinochloa crusgalli* (BG); oat, *Avena sativa* (O); linseed, *Linum usitatissimum* (L); mustard, *Sinapis alba* (M); sugar beet, *Beta vulgaris* (SB) and soya bean, *Glycine max* (S). The tests conducted were foliar spray tests, in which seedling plants were sprayed with a formulation containing the test compound.

The soil used in the tests was a prepared horticultural loam.

The formulations used in the tests were prepared by diluting with water, solutions of the test compounds in acetone containing 0.4% by weight of an alkylphenol-/ethylene oxide condensate available under the trade name TRITON X-155. The acetone solutions were diluted with an equal volume of water and the resulting formulations applied at a dosage level corresponding to 5 kilograms active material per hectare in a volume equivalent to 650 liters per hectare. Untreated seedlings plants were used as controls.

The herbicidal effects of the test compounds were assessed visually eleven days after spraying the foliage and were recorded on a 0–9 scale. A rating 0 indicates growth as untreated control, a rating 9 indicates death. An increase of 1 unit on the linear scale approximates to a 10% increase in the level of effect.

The results of the tests are set out in Table II below.

TABLE II

| Compound of Example No. | Herbicidal Activity Phytotoxicity Rating Foliar Spray | | | | | | | |
|---|---|---|---|---|---|---|---|---|
| | Mz | R | BG | O | L | M | SB | S |
| 1 | 7 | 4 | 7 | 5 | 8 | 7 | 8 | 8 |
| 2 | 2 | 2 | 5 | 4 | 7 | 7 | 4 | 7 |
| 3 | 4 | 5 | 6 | 6 | 7 | 6 | 6 | 5 |
| 4 | 3 | 3 | 6 | 5 | 7 | 6 | 5 | 7 |
| 5 | 4 | 5 | 5 | 6 | 6 | 5 | 6 | 5 |
| 6 | 5 | 4 | 6 | 6 | 7 | 6 | 6 | 6 |
| 7 | 4 | 0 | 7 | 3 | 7 | 7 | 7 | 7 |
| 8 | 2 | 0 | 6 | 3 | 6 | 6 | 5 | 7 |
| 9 | 0 | 0 | 0 | 0 | 6 | 6 | 5 | 7 |
| 10 | 3 | 0 | 4 | 4 | 4 | 4 | 5 | 5 |
| 11 | 4 | 4 | 7 | 5 | 6 | 6 | 6 | 7 |
| 12 | 0 | 0 | 5 | 5 | 5 | 5 | 6 | 7 |
| 13 | 5 | 5 | 6 | 6 | 8 | 6 | 7 | 6 |
| 14 | 4 | 0 | 7 | 5 | 5 | 7 | 5 | 6 |
| 15 | 3 | 0 | 8 | 0 | 4 | 5 | 4 | 6 |
| 16 | 4 | 0 | 7 | 4 | 5 | 5 | 5 | 5 |
| 17 | 4 | 0 | 5 | 3 | 5 | 5 | 4 | 5 |
| 18 | 4 | 2 | 7 | 3 | 7 | 5 | 5 | 6 |
| 19 | 5 | 4 | 6 | 5 | 7 | 6 | 6 | 7 |

In addition to the foliar spray tests, pre-emergence tests were carried out in which soil planted with seeds of the various plant species was treated with a compound according to the invention. All of the compounds of Examples 1–19 showed pre-emergence herbicidal activity.

EXAMPLE 21

Plant Growth Regulating Activity

Observations were made throughout the tests described in Example 21 of the precise effects on the test plants of the compounds of the invention. The following effects were observed.

1. All the compounds showing activity in the herbicide tests produced a depression in growth—i.e. a reduction in stem height—for some or all of the plant species.

2. Many of the compounds resulted in hyperchromism in the test plants—i.e. the production of very dark green leaves.

Various other symptoms were observed in various tests, including the production of enlarged cotyledons, the production of shortened internodes, and the production of shorter, broader leaves.

EXAMPLE 22

Plant Growth Regulating Activity

The compound of Example 1 was examined in detail for plant growth regulating properties as follows.

Seeds of various plant species were planted and treated with various dosages of 1:1 v/v acetone/water solution of the test compound. The resulting growth was evaluated at weekly intervals up to at least five weeks from spraying. With the grass species, the growth was harvested at intervals and the fresh weight was recorded. All tests were conducted using untreated plants as control.

The plant species tested were as follows:

Maize; Grain Sorghum; Wheat; Barley; Oat Cultivated; Oat Wild; Ryegrass; Tall fescue; Blackgrass; Barnyard grass; Browntop bent; Couchgrass; Bermuda grass; Nutsedge; Convolvulus; Soya bean; Sugar beet; Cotton; Lucerne; Kale; Velvet leaf; Mustard; Redshank; Cleavers; Pale persicaria; Plantain; Corn Marigold; Spurrey; Shepherds Purse; Mayweed; Purslane; Pigweed.

The test compound had significant growth-regulating activity against every species with the exception of nutsedge. The main symptoms produced were depression (reduced plant height), hyperchromism (dark green leaves), reduced internode length (leaves closer together on the stem), and some of the grasses had expanded leaves (leaves on treated plants were short and broad compared with those on untreated plants which were longer and thinner).

The overall effect was compacting of the growth.

The fresh weights of the harvested growths showed that the growth, compared with untreated controls, was much reduced, and that the effect was long-lasting. Further tests showed that the effect could be removed and normal growth re-established by treatment with the plant hormone gibberellic acid.

EXAMPLE 23

Chemical Lawn Mower

The effect of the compound of Example 1 on the growth of various grasses, was compared with the effect of maleic hydrazide, a commercial growth retardant.

The grasses Barren Brome (*Bromus sterilis*, BB), Yorkshire Fog (*Holcus lanatus*, YO), Tall fescue (*Festuca arundinacea*, TF), Common Bent (*Agrostis tenuis*, BT) and Perennial Ryegrass (*Lolium perenne*, LP) were propagated in plastic trays to produce turf which was cut back and allowed to grow five times before treatment.

The compound of Example 1 was formulated as a solution in acetone/water (25:75 v:v) containing 0.2% Triton X 155 (Trade Mark) as surface active agent, and applied to the test species as a root drench at dosages corresponding to 5.0, 2.5 and 1.0 kilograms per hectare. For comparison, maleic hydrazide formulated as an aqueous solution containing 0.2% Triton X 155 (Trade Mark), was applied at the same dosages, but as a foliar spray, the form of application recommended commercially.

Two types of assessment were made.

(a) effect on visual appearance of the turf.

Visual assessments were made 25 days after treatment. Rating was on a linear 0–9 scale, 0 indicating excellent appearance and 9 indicating a completely unacceptable appearance. The results were converted into a percentage of control, results greater than 100 indicating that the treated species had a more pleasing appearance than the untreated control plants.

(b) effects on cutting frequency

The commercial recommendations for maleic hydrazide state that one mowing is usually required after treatment, before chemical effects on growth rate become apparent. Grasses in the untreated trays of all the species had reached a suitable cutting height eleven days after treatment. After measuring the heights all the grasses were cut back to the tops of the trays, these being generally 15 millimeters above soil level. After this first cut the grasses were allowed to grow unchecked until they had reached the original cutting height of the untreated control turves. The cutting height of the species differed according to their growth rates and were as follows:

| | |
|---|---|
| Barren Brome | 100 |
| Yorkshire Fog | 70 |
| Tall Fescue | 60 |
| Common Bent | 40 |
| Perennial Ryegrass | 60 |

These heights were considered fairly realistic, lawns containing common bent usually being kept shorter than roadsides covered in coarse grasses.

The number of days required to reach the cutting height was recorded.

It was found that the compound of Example 1 produced a most attractive dark green sward. Maleic hydrazide, on the other hand, produced symptoms of chlorosis and necrosis, severely weakening the plants. In one test, all the test plants died.

TABLE III

| Compound Tested | Dosage Kg/ha | Visual Appearance % of control, greater than 100 indicates improved appearance | | | | | Number of Days before cutting required | | | | |
|---|---|---|---|---|---|---|---|---|---|---|---|
| | | BB | YO | TF | BT | LP | BB | YO | TF | BT | LP |
| Compound of | 5.0 | 118 | 108 | 117 | 123 | 118 | 42 | 30 | 31 | 22 | 34 |
| Example 1 | 2.5 | 114 | 122 | 117 | 119 | 114 | 34 | 29 | 29 | 20 | 31 |
| | 1.0 | 100 | 101 | 100 | 109 | 100 | 29 | 24 | 19 | 14 | 17 |
| Maleic | 5.0 | 41 | 21 | 67 | 17 | 31 | 34 | + | 35 | 22 | 31 |
| Hydrazide | 2.5 | 92 | 38 | 77 | 71 | 83 | 17 | 24 | 27 | 20 | 27 |
| | 1.0 | 97 | 93 | 96 | 97 | 97 | 14 | 17 | 19 | 14 | 14 |
| Control | — | 100 | 100 | 100 | 100 | 100 | 14 | 14 | 14 | 14 | 14 |

+ = complete death of all treated plants.

These results show the compound of Example 1 to be much more useful as a "chemical lawn mower" than maleic hydrazide.

We claim as our invention:

1. A method for reducing the growth of a plant which comprises subjecting the plant to an effective dosage of a compound of the formula:

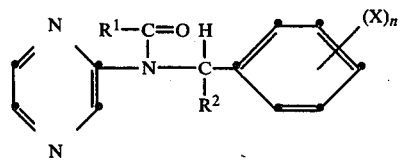

wherein $R^1$ is hydrogen, or is alkyl, alkoxyalkyl, cycloalkyl or alkylcycloalkyl of up to six carbon atoms, $R^2$ is hydrogen or alkyl of one to four carbon atoms, X is halogen or alkyl of from one to six carbon atoms and n is one or two, and the horticulturally acceptable acid addition salts, and complexes thereof with halides of calcium, copper and iron.

2. A method according to claim 1 wherein the compound is the one wherein $R^1$ is tertiary-butyl, $R^2$ is hydrogen and $(X)_n$ is 4-chloro.

* * * * *